(12) United States Patent
Scorsone et al.

(10) Patent No.: US 11,534,095 B2
(45) Date of Patent: Dec. 27, 2022

(54) FLEXIBLE SOFT DIAMOND IMPLANT

(71) Applicants: Chambre de Commerce et D'Industrie de Region Paris Ile de France, Noisy le Grand (FR); COMMISSARIAT A L'ENERGIE ATOMIQUE ET AUX ENERGIES ALTERNATIVES, Paris (FR)

(72) Inventors: Emmanuel Scorsone, Magny-les-Hameaux (FR); Lionel Rousseau, Le Perreux-sur-Marne (FR)

(73) Assignees: Chambre de Commerce et D'Industrie de Region Paris Ile de France; COMMISSARIAT A L'ENERGIE ATOMIQUE ET AUX ENERGIES ALTERNATIVES

( * ) Notice: Subject to any disclaimer, the term of this patent is extended or adjusted under 35 U.S.C. 154(b) by 299 days.

(21) Appl. No.: 16/759,172

(22) PCT Filed: Oct. 25, 2018

(86) PCT No.: PCT/EP2018/079353
§ 371 (c)(1),
(2) Date: Apr. 24, 2020

(87) PCT Pub. No.: WO2019/081683
PCT Pub. Date: May 2, 2019

(65) Prior Publication Data
US 2021/0177333 A1    Jun. 17, 2021

(30) Foreign Application Priority Data
Oct. 25, 2017 (FR) ...................................... 1760074

(51) Int. Cl.
*A61N 1/05*     (2006.01)
*A61B 5/263*    (2021.01)
(Continued)

(52) U.S. Cl.
CPC .............. *A61B 5/263* (2021.01); *A61B 5/279* (2021.01); *A61N 1/0531* (2013.01); *C30B 25/02* (2013.01); *C30B 29/04* (2013.01)

(58) Field of Classification Search
CPC .... A61N 1/0531; A61N 1/0543; A61B 5/263; C30B 29/04
See application file for complete search history.

(56) References Cited

U.S. PATENT DOCUMENTS

2002/0120296 A1 * 8/2002 Mech ................... C23C 16/278
607/54
2011/0162962 A1    7/2011 Mazellier
(Continued)

FOREIGN PATENT DOCUMENTS

| EP | 2343543 A1 | 7/2011 |
| FR | 2960787 A1 | 12/2011 |
| FR | 3011727 A1 | 4/2015 |

OTHER PUBLICATIONS

International Search Report for PCT/EP2018/079353 dated Jan. 21, 2019; 2 pages.
(Continued)

*Primary Examiner* — George R Evanisko
(74) *Attorney, Agent, or Firm* — Lerner, David, Littenberg, Krumholz & Mentlik, LLP

(57) ABSTRACT

Flexible implant for electrically recording or stimulating a nerve structure, said flexible implant comprising: a first layer of electrically insulating diamond; an electrode of electrically conductive doped diamond, in contact with the first layer of electrically insulating diamond; an electrically conductive layer in contact with the electrode and the first layer, so as to define a conductive track for the electrode; and a second layer of electrically insulating diamond, at least in contact with the electrically conductive layer and a remaining portion of the first layer, all of the above arranged such
(Continued)

that: electrically insulating diamond/electrically conductive doped diamond sealing is provided at the electrode (3) by resumption of epitaxial growth; and the electrically conductive layer is encapsulated by the electrode (3), the first layer and the second layer, at the electrode and over the entirety of the remaining surface thereof except over an area defining an electrical contact. The implant has two faces, namely: a front face comprising one of the two layers of electrically insulating diamond, open locally, providing access to the electrode and the area defining an electrical contact; and a rear face comprising the other of the two layers of electrically insulating diamond.

18 Claims, 20 Drawing Sheets

(51) Int. Cl.
*A61B 5/279* (2021.01)
*C30B 25/02* (2006.01)
*C30B 29/04* (2006.01)

(56) References Cited

U.S. PATENT DOCUMENTS

2013/0228547 A1 9/2013 Scorsone et al.
2016/0287113 A1 10/2016 Hebert et al.

OTHER PUBLICATIONS

Minnikanti S, Diao G, Pancrazio JJ, Xie X, Rieth L, Solzbacher F, Peixoto N. Lifetime assessment of atomic-layer-deposited Al2O3-Parylene C bilayer coating for neural interfaces using accelerated age testing and electrochemical characterization. Acta biomaterialia. Feb. 1, 2014;10(2):960-7.
Seymour JP, Elkasabi YM, Chen HY, Lahann J, Kipke DR. The insulation performance of reactive parylene films in implantable electronic devices. Biomaterials. Oct. 1, 2009;30(31):6158-67.
Lei X, Kane S, Cogan S, Lorach H, Galambos L, Huie P, Mathieson K, Kamins T, Harris J, Palanker D. SiC protective coating for photovoltaic retinal prosthesis. Journal of neural engineering. Jun. 21, 2016;13(4):046016.
Sterken T, de Beeck MO, Torfs T, Vermeiren F, Van Hoof C, Vanfleteren J. Embedded UTCP interposers for miniature smart sensors. InIMAPS medical applications workshop, Paris Dec. 4, 2012.

\* cited by examiner

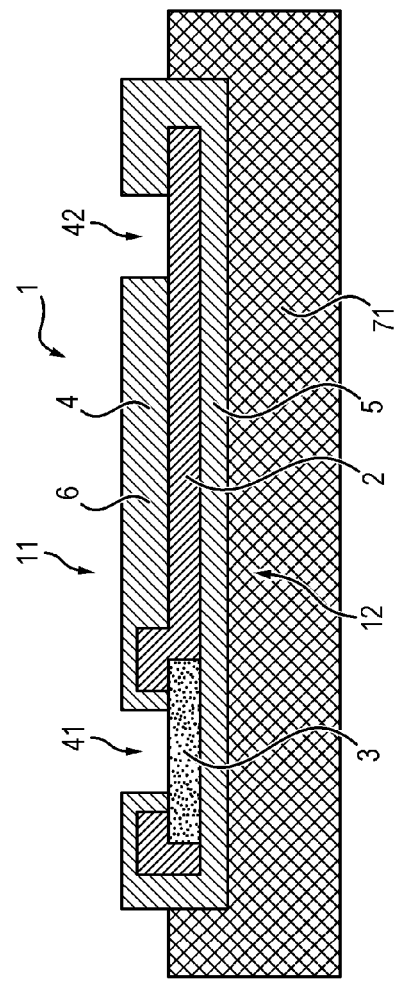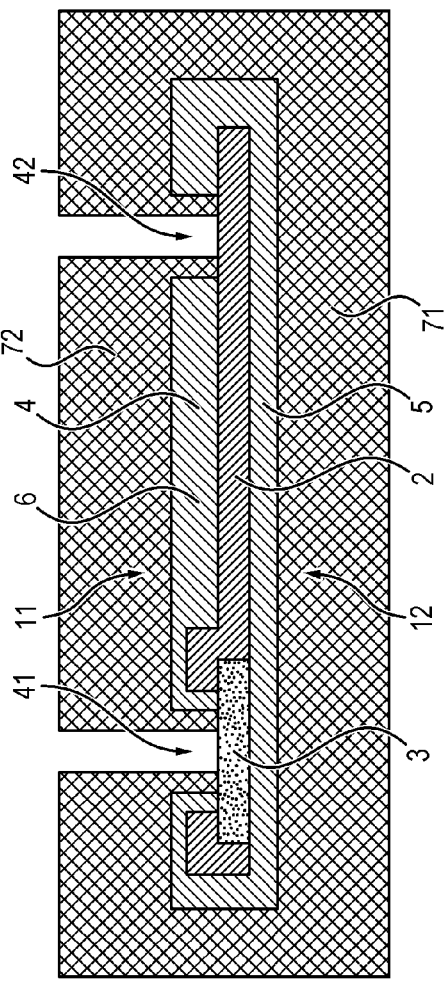

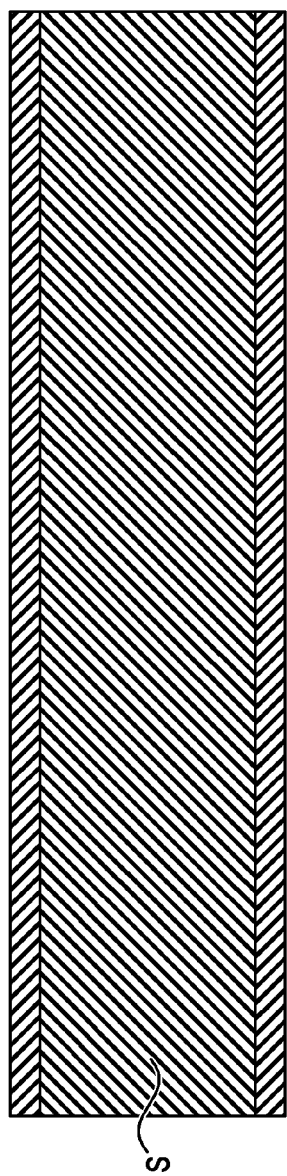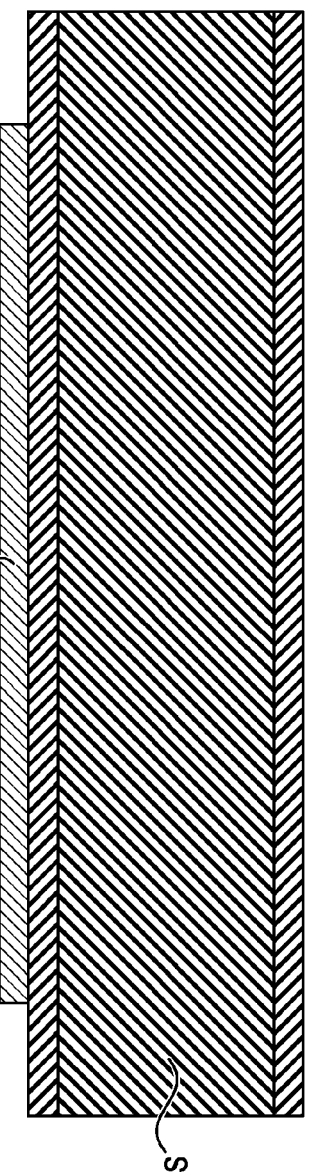

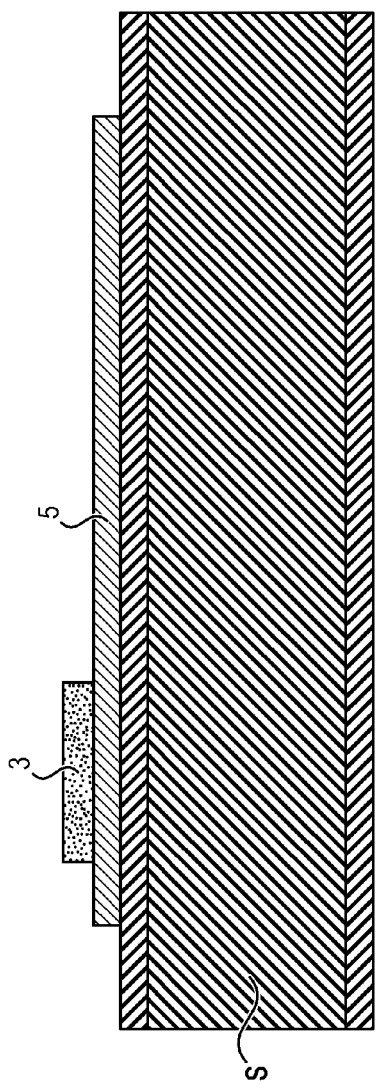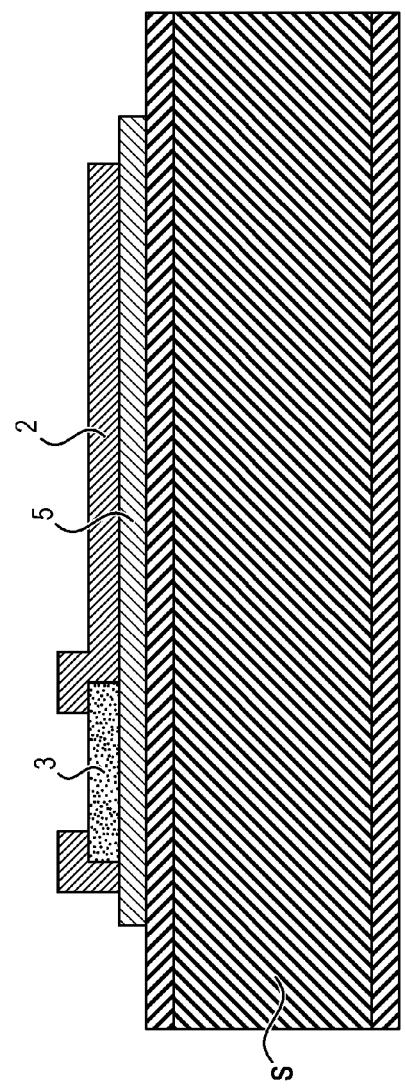

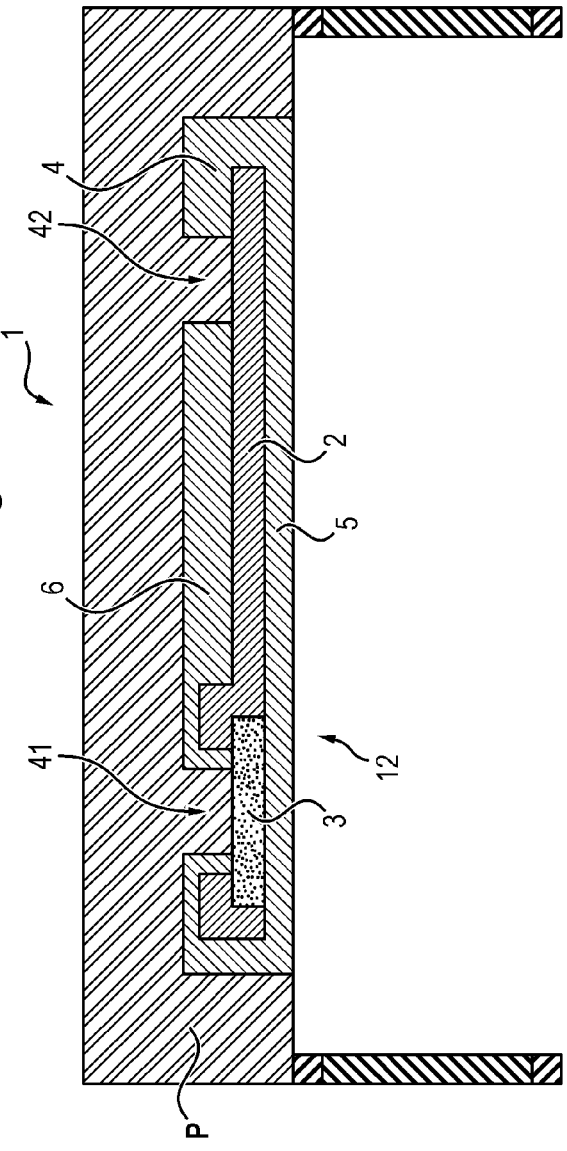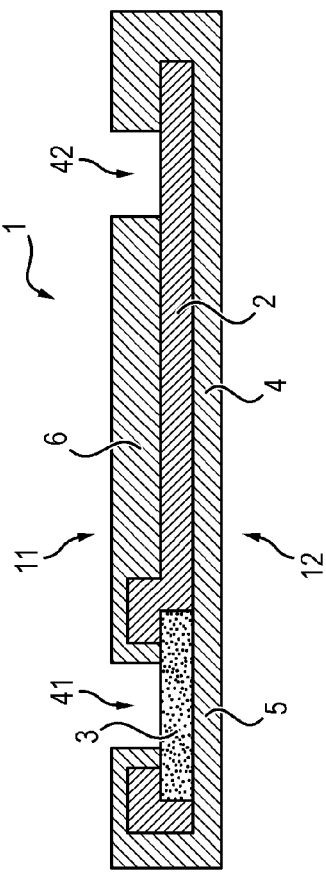

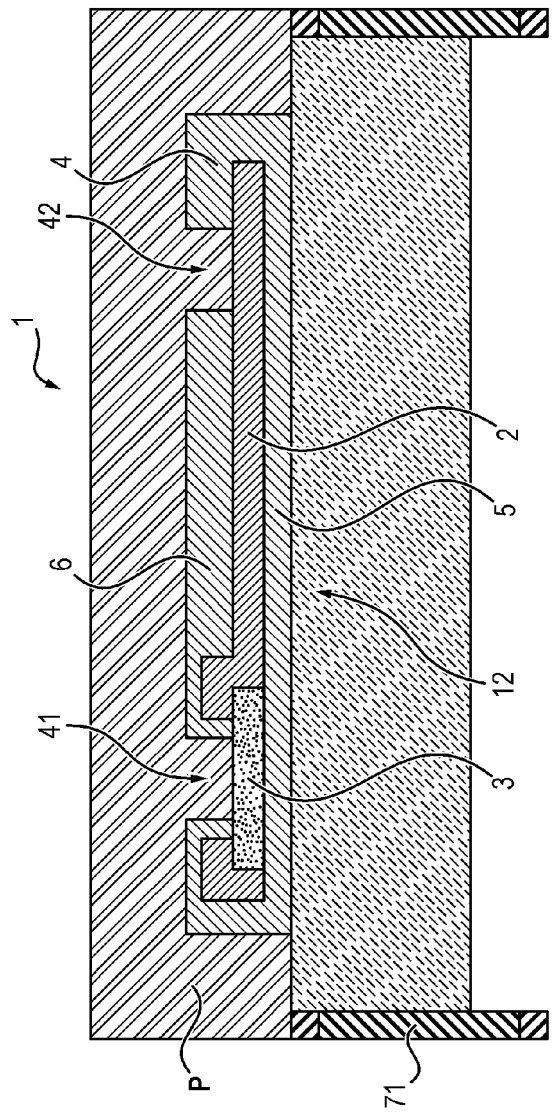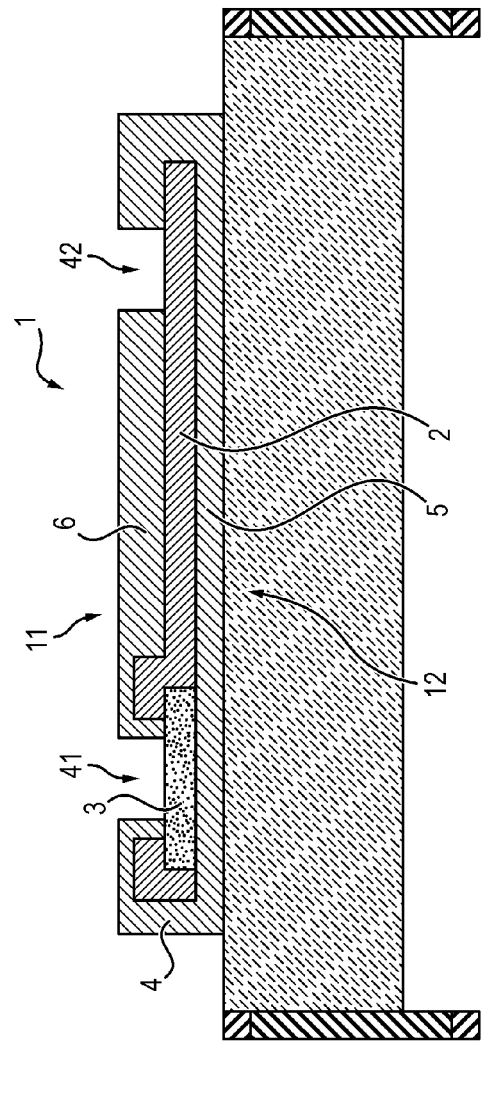
FIG. 9a
FIG. 9b

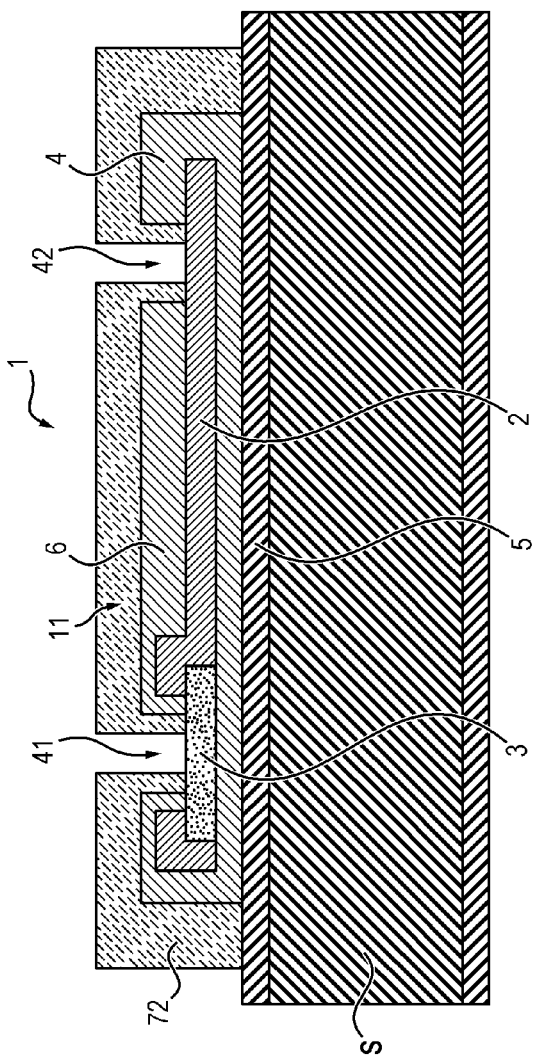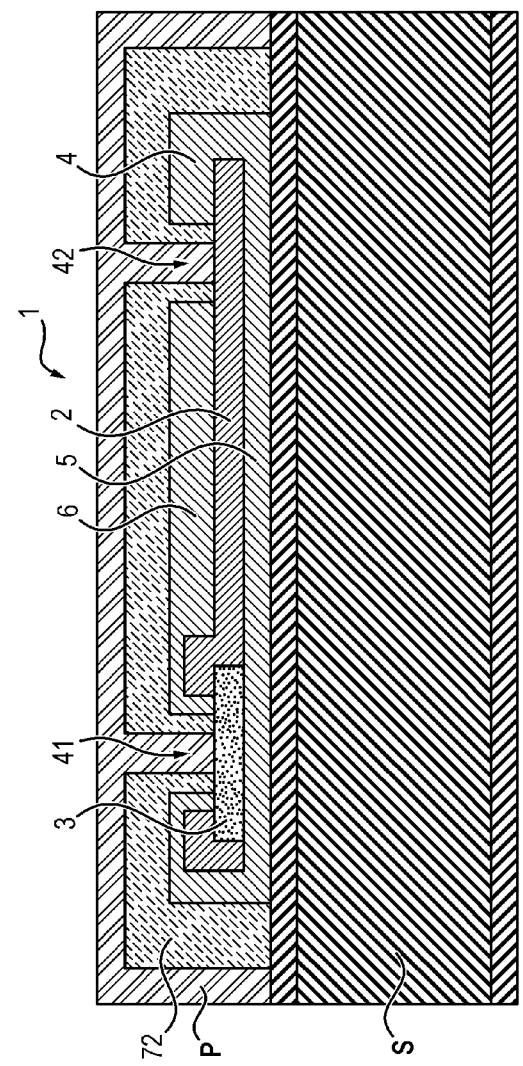
FIG. 10a
FIG. 10b

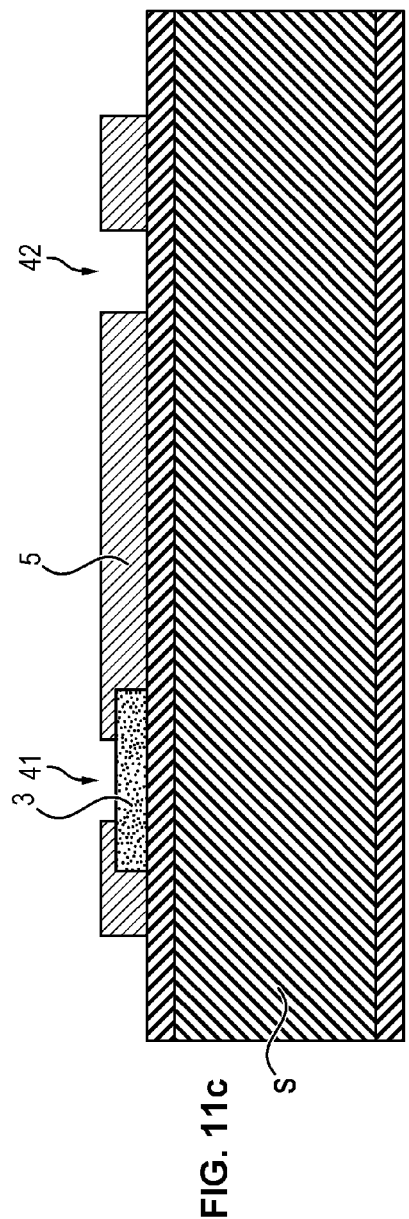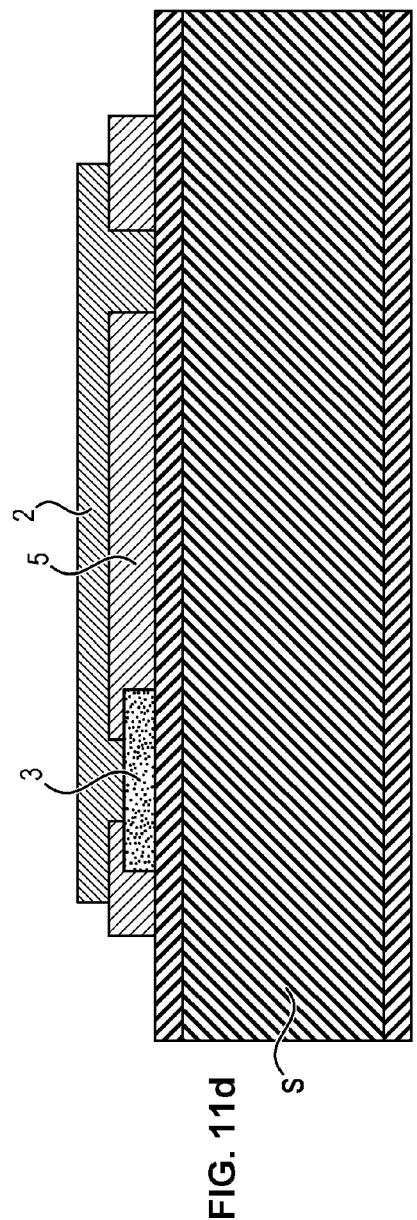

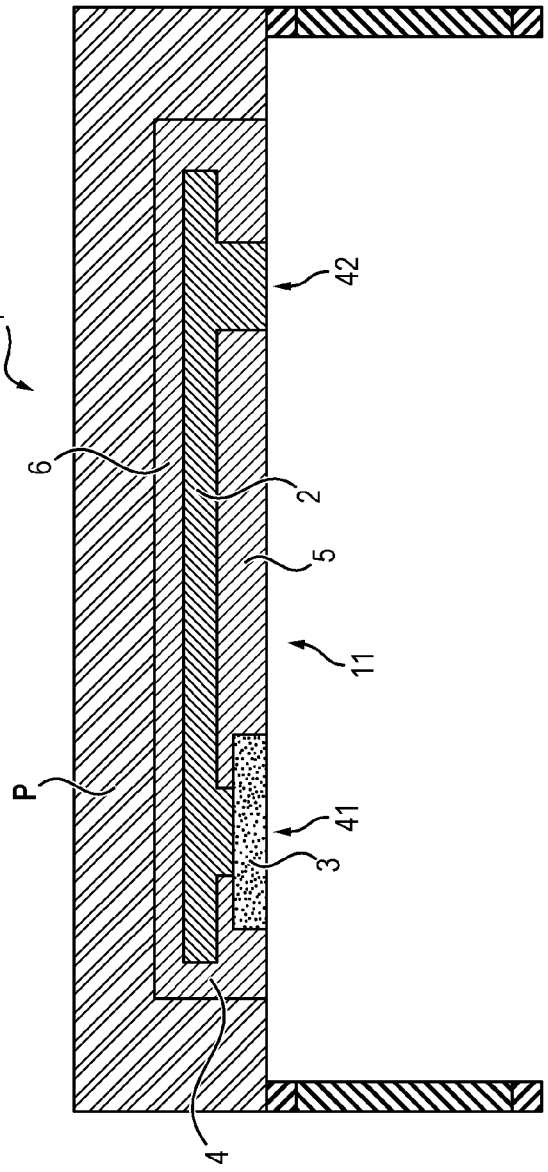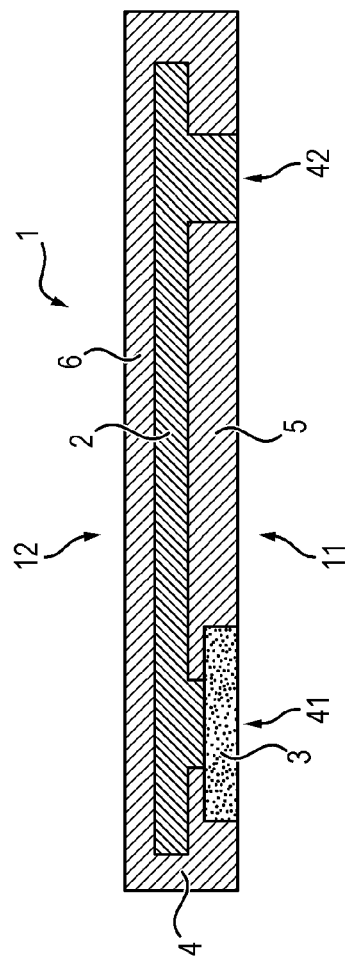

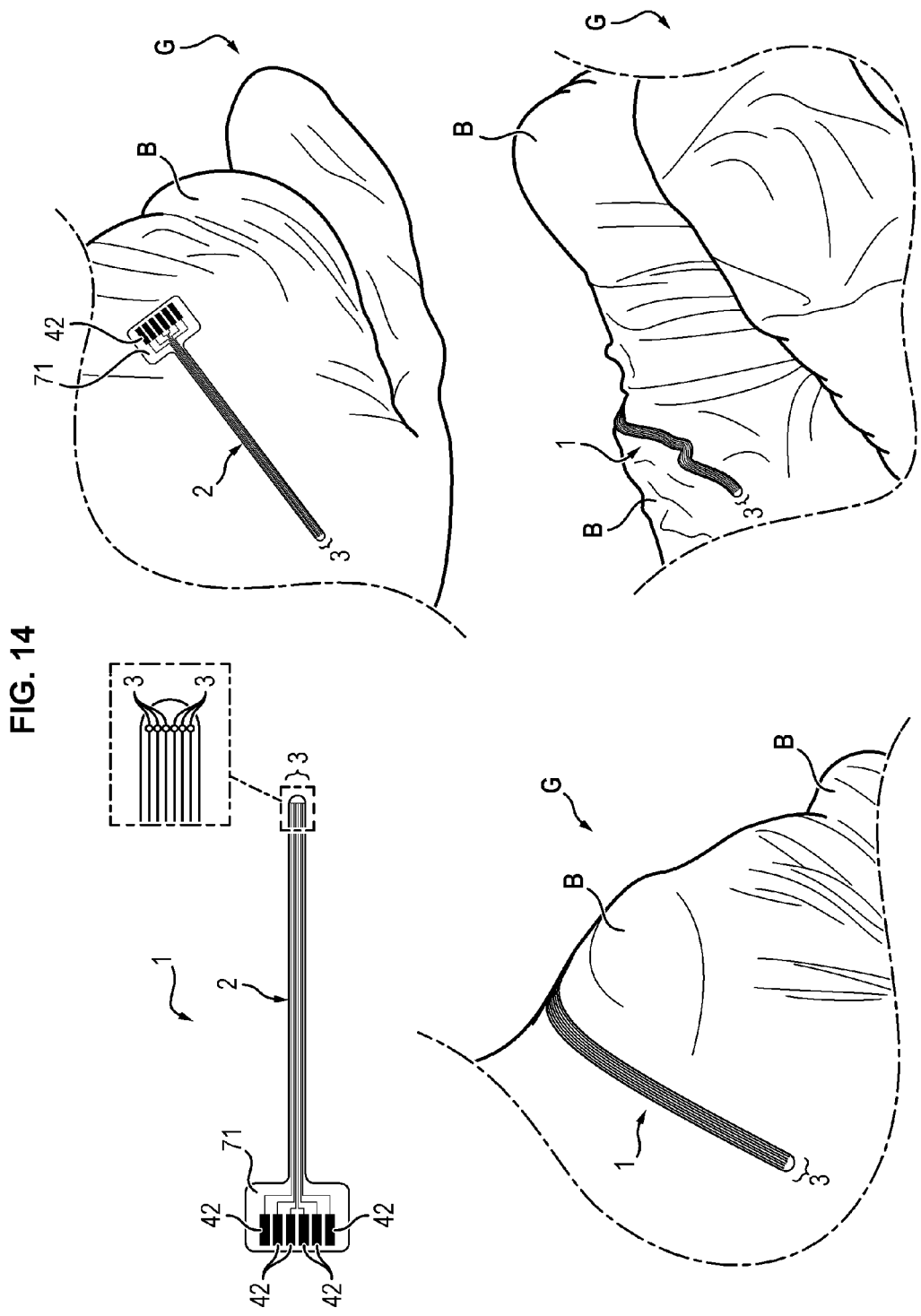

FLEXIBLE SOFT DIAMOND IMPLANT

CROSS-REFERENCE TO RELATED APPLICATIONS

The present application is a national phase entry under 35 U.S.C § 371 of International Application No. PCT/EP2018/079353 filed Oct. 25, 2018, which claims priority from French Application No. 1760074 filed Oct. 25, 2017, all of which are hereby incorporated herein by reference.

FIELD OF THE INVENTION

The present invention relates to implants intended to be installed on a nerve structure, in particular in order to stimulate said nerve structure or to measure the electrical signals emitted by said nerve structure.

The invention applies in particular to retinal or cortical implants.

The invention also relates to a process for manufacturing such implants.

PRIOR ART

It is now possible, thanks to implants, to restore certain failing functions in patients.

It is thus possible, for example, to restore sight to patients suffering from age-related macular degeneration (AMD) or pigmentary retinopathy (PR).

For this purpose, there are now electronic systems, or so-called "retinal implants", which are implanted in the retina of patients suffering from these diseases.

These electronic systems, or implants, which are implanted in the patient's body include microelectrodes that stimulate the cells of the retina when they come into contact with it.

Other implants under development are cortical (or electrocorticographic, ECoG) implants, which are intended to be placed directly on the surface of the patient's brain (cortex).

This next generation of implants should enable even further functional rehabilitation.

One goal is in particular to enable patients with non-functional optic nerves to regain their sight with this new generation of implants, which is not currently the case with existing retinal implants.

Patients targeted by the new generation of implants include patients with glaucoma disease. By 2020, glaucoma will affect 80 million people worldwide (figures from a study in the British Journal of Ophthalmology) and 9% of those affected will lose their sight completely.

Moreover, the use of these implants is not limited to blind patients only, but can also concern quadriplegic or paraplegic patients in order to regain autonomy.

The aim of this new generation of implants is to create real interfaces with the brain so that these patients can interact with the world around them. These are called brain-computer interfaces (BCI).

The role of the implants is then to record or stimulate neuronal activities, a decoding of this information being carried out to control different systems (chair, robotic arm, etc.).

Clinical applications can also be considered for patients in coma or affected by motor deafferentation syndrome (lock-in syndrome).

For these patients who no longer have any motor function that allows them to communicate with the outside world, these prostheses would allow them to come and communicate with them to know their condition and improve knowledge about these pathologies for better therapy.

With the development of these applications, one of the real challenges for this future generation of implants is the lifespan of these implants. Indeed, the implantation of these implants in the body requires very complex surgery. It is preferable that an implant once implanted does not require frequent replacement.

The goal is therefore to obtain implants that can remain implanted in a patient's body between 5 and 20 years. Currently, however, the certifications given for cortical implants do not exceed 30 days.

In addition, the implants must have a high degree of flexibility in order to be able to adapt to the shape of the organ on which said implants are installed and not to damage the organ on which said implants are installed (glial reaction in contact with the implants). The flexibility of the implant must be particularly high when the implant is intended to be implanted in the brain of a patient, the brain being an organ with a particularly uneven surface.

Today's flexible soft implants are composed of two layers of polymer that surround and thus isolate the metal tracks from the aqueous medium. The polymer layers have the advantage of forming a protective layer that is flexible enough to allow the implant to conform to the shape of the organ on which it is implanted.

However, a problem encountered by these flexible soft implants is that no polymer is impermeable in the long term, and that the metal layers of the implants degrade over time, creating implant drift and a change in the performance of the implants over time following implantation.

A first known technique to improve the impermeability of such flexible soft implants is to increase the thickness of the polymer layers. However, such an increase in the thickness of the polymer layers reduces the flexibility of the implants.

A second known technique to improve the impermeability of flexible soft implants consists in making barrier layers on the metal tracks by atomic layer deposition (ALD). Typically, the deposited barrier layers can be $Al_2O_3$, $TiO_2$ or SiC. These barrier layers are then covered by polymer layers. This second technique is notably described in the documents "M. Saugandhika et al., Acta Biomatetialia, 960-967, 2014", "JP Seymour et al., Biomaterials 6158,6167, 2009 X", "Lei et al., Journal of Neural Engineering. 2016 0.1088/1741-2560/13/4/046016, 2016", and "M. Op de beeck, IMAPS Workshop Dec. 2012".

Thus, as shown in FIG. 1, an implant 1' according to this second technique comprises a metal core 2' that forms a metal track 3' on the one hand and an electrode 4' on the other. The electrode 4' is formed by the fact that the metal core 2' is not covered at the electrode 4', unlike the metal track 3'. As mentioned above, the metal track 3' is surrounded by barrier layers 5', said barrier layers 5' themselves being surrounded by polymer layers 6'.

However, as shown in FIG. 1, this second technique encounters an impermeability problem at the electrode 4'. Indeed, the implant 1' has a weak area 7' because part of the metal core 2' of the implant 1' is not covered by the barrier layers 5', and only by the polymer layers 6'.

General Presentation of the Invention

An aim of the invention is to provide a solution enabling an implant to be implanted in the body of a patient, typically directly on the patient's cortex, which has both a great flexibility to be able to fit the shape of the organ which may have folds and on which the implant is intended to be implanted, and a very long life once implanted in the patient's body.

Another aim of the invention is to obtain an implant with a high signal-to-noise ratio.

For this purpose, according to a first aspect of the invention, a flexible soft implant is provided for the focal stimulation or electrical recording of a nerve structure of an organ of interest, comprising:
- a first layer of electrically insulating diamond,
- at least one electrically conductive doped diamond electrode in contact with the first electrically insulating diamond layer,
- an electrically conductive layer in contact with:
  - the electrode, and
  - the first layer,
  to define a conductive track per electrode;
- a second electrically insulating diamond layer at least in contact with the electrically conductive layer and a remaining part of the first layer, arranged in such a way that:
- an electrically insulating diamond/electrically conductive doped diamond seal is produced at the electrode by epitaxial regrowth,
- the electrically conductive layer is encapsulated by the electrode, by the first layer, and by the second layer, at the electrode, and by the first layer, and by the second layer over its entire remaining surface except for an area defining an electrical contact by electrode, the flexible soft implant having two sides:
- a front side comprising one of the two electrically insulating diamond layers which is locally open, allowing access to the electrode and to the area defining an electrical contact for the electrode;
- a back side having the other of the two electrically insulating diamond layers.

This implant is advantageously complemented by the following features taken alone or in all their technically possible combinations:
- the total thickness and geometry of the implant are adapted so that the implant fits the surface of the organ of interest, such as the cortex, the heart, or a muscle, the total thickness of the implant being less than 20 µm; advantageously it can be less than 10 µm;
- at the electrode, the electrically conductive layer is encapsulated by the electrode and the second layer is produced by epitaxial regrowth from the electrode, the electrode being encapsulated, except for a central measuring part, by the first layer, the second layer and the electrically conductive layer;
- the electrically conductive layer is encapsulated by the electrode and the first and second layers, the first layer being made by epitaxial regrowth from the electrode;
- the first layer, the electrode, and the second layer each have thicknesses of less than one micrometer, advantageously 500 nm;
- the electrically conductive layer has a thickness of less than 3 µm;
- the implant has at least one outer layer of biocompatible polymer;
- the implant has a first outer polymer layer on the back side of the implant;
- the implant has a second outer polymer layer on the front side of the implant except at at least one measuring part of the electrode and at an electrical contact area,
- the implant is thus completely encapsulated by polymer, except for the measuring part of the electrode and the electrical contact area;
- the outer polymer layer(s) has (have) a thickness of between 2 and 10 µm;
- the polymer is a biodegradable polymer;
- the doped diamond electrode is nanostructured;
- the diamond of the following elements: electrode, first layer, second layer, and electrically conductive layer when made of diamond,
  is not ultrananocrystalline (UNCD);
- the diamond for the electrode is doped with boron or phosphorus;
- the ratio of the length of the opening at the electrode and the opening at the track to the thickness of the implant is greater than 100

The invention also provides a process for manufacturing at least one flexible soft implant for the focal stimulation or electrical recording of a nerve structure of an organ of interest, of the aforementioned type, said implant being made by the following steps from a substrate S:
- (S1) producing a first electrically insulating diamond layer and at least one electrode made of electrically conductive doped diamond by epitaxial growth, the electrode and the first layer being deposited one on top of the other by epitaxial regrowth at the end of this step (S1);
- (S2) depositing an electrically conductive layer supported on at least a portion of the electrode and at least a given portion of the first layer, to define a conductive track per electrode;
- (S3) forming a second layer supported on at least part of the electrically conductive layer and at least on a remaining part of the first layer (which has a free surface) by epitaxial growth; the steps of the process are carried out so that:
- an electrically insulating diamond/electrically conductive doped diamond seal is produced at the electrode by epitaxial regrowth,
- the electrically conductive layer is encapsulated by the electrode, by the first layer, and by the second layer, at the electrode and over its entire remaining surface except for an area defining an electrical contact.

The process is advantageously complemented by the following features taken alone or in all their technically possible combinations:
- the total thickness of the flexible soft implant is less than 20 µm;
- the process comprises the following steps:
  - in step (S1), producing the first electrically insulating diamond layer on the substrate S by epitaxial growth, then producing at least one electrically conductive doped diamond electrode supported on the first layer by epitaxial regrowth,
  - in step (S2), depositing the electrically conductive layer on an outer contour of the electrode and at least on a given part of the first layer,
  - in step (S3), epitaxial growth of the second layer is performed on:
  - the electrically conductive layer except on an area defining an electrical contact per conductive track, as well as on the electrode by epitaxial regrowth, leaving a central measuring part of the electrode open to the air,
  - this regrowth of electrically insulating diamond on electrically conductive doped diamond guarantees the impermeability of the implant at the electrode;

the process comprises the following steps:
- in step (S1), producing at least one electrically conductive doped diamond electrode on the substrate S by epitaxially growth,
- then making the first diamond layer on the outer contour of the electrode by epitaxial regrowth and on part of the substrate S by epitaxial growth except in a given area which defines an electrical contact,
- in step (S2), depositing the conductive layer on at least a central part of the electrode, on at least a given part of the first layer to make one conductive track per electrode, and on the given area of electrical contact to make one electrical contact per conductive track;

the process comprises the following additional step (S4) of depositing at least one outer polymer layer, for example on the back side of the implant;

the process comprises the following additional steps:
- (S41) depositing an outer polymer layer on the front side of the implant, where the electrode and the associated electrical contact are located, and on the substrate S;
- (S42) opening the outer polymer layer at the electrical contact and the electrode and depositing a protective resin;
- (S43) etching the substrate until the back side of the implant is exposed;
- (S44) depositing another outer polymer layer on the back side of the implant, removal of the protective resin and cutting of the implant to give it its final shape;

the electrode is nanostructured as follows:
- a material forming a nanostructured 3D pattern is deposited on the electrode;
- an electrically conductive doped diamond layer is deposited over the material forming the nanostructured pattern.

PRESENTATION OF THE FIGURES

Other features, purposes and advantages of the invention will appear upon reading the following description of different embodiments represented in the following drawings which are not at full scale, the implant being much longer than it is thick:

FIG. 3a shows an implant according to the first embodiment comprising a polymer layer on its back side;

FIG. 3b represents an implant according to the first embodiment comprising a polymer layer on its back side and a polymer layer on its front side;

Figure 7:
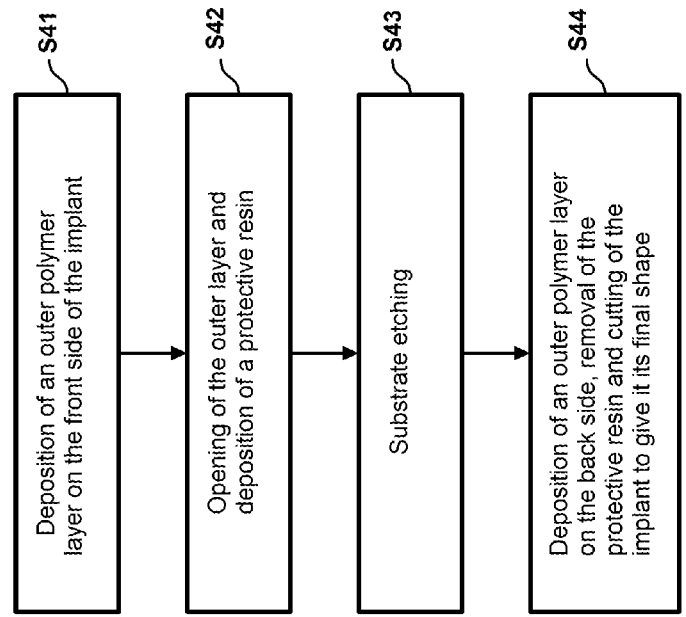
Figure 12:
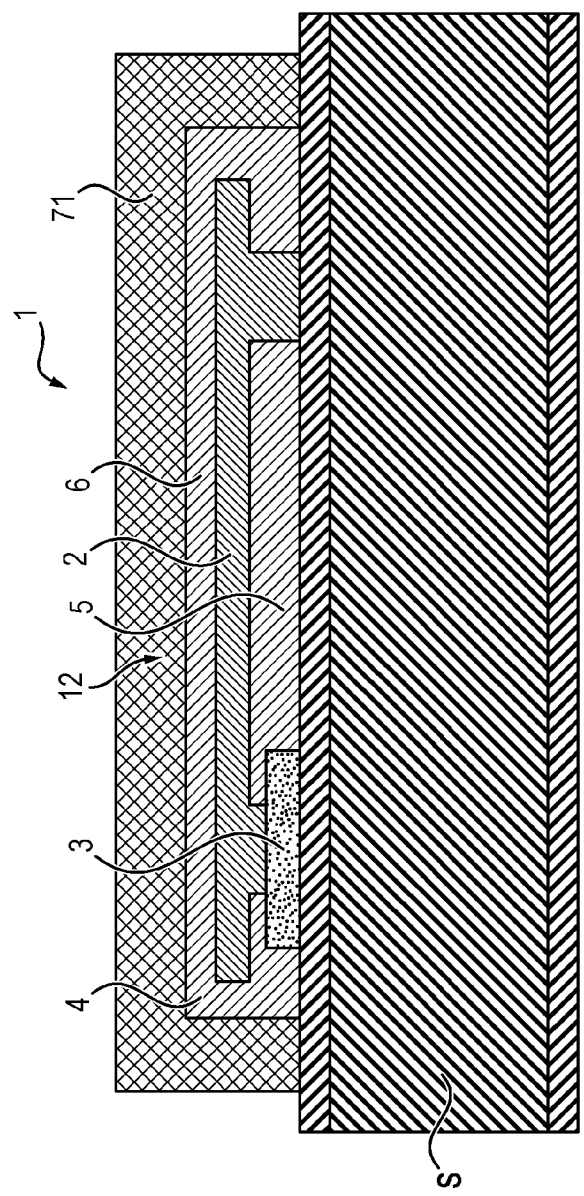

FIG. 7 schematically shows the steps of a variant of the manufacturing process for depositing polymer layers on the front side and on the back side of the implant;

FIGS. 8a, 8b, 8c, 8d, 8e, 8f, 8g, and 8h represent the different states of the implant during the different steps of the manufacturing process according to a first possible implementation for the realization of an implant according to the first embodiment of the invention, the implant being here only made of diamond+metal (without polymer coating) and self-supporting;

FIGS. 9a and 9b show different implant states during the steps of depositing a polymer layer only on the back side of the implant in a possible variant of the first implementation of the manufacturing process;

FIGS. 10a, 10b, 10c, 10d and 10e represent different implant states during the steps of depositing a polymer layer on the front side and the back side of the implant in a possible variation of the first implementation of the manufacturing process;

FIGS. 11a, 11b, 11c, 11d, 11e, 11f, 11g, and 11h represent the different states of the implant during the different steps of the manufacturing process according to a second possible implementation for the realization of an implant according to the second embodiment of the invention;

FIG. 12 shows an intermediate state of the implant during a step of depositing a polymer layer on the back side of the implant according to a variant of the second possible implementation of the manufacturing process;

FIGS. 13a-13g represent top views of the different states of the implant according to the first embodiment during its manufacture;

FIG. 14 represents an implant according to the invention disposed on a latex glove whose surface simulates the surface of a nerve structure on which the implant is intended to be implanted.

DESCRIPTION OF THE INVENTION

Figure 1:
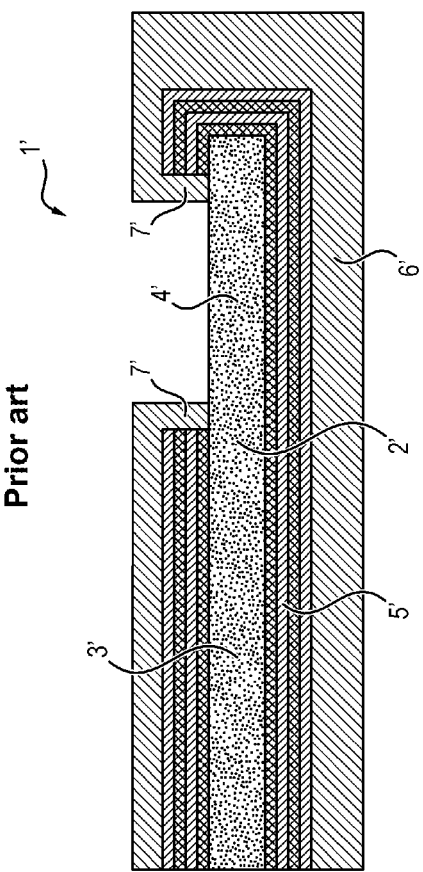
FIG. 1 shows an implant according to the prior art.
Figure 2:
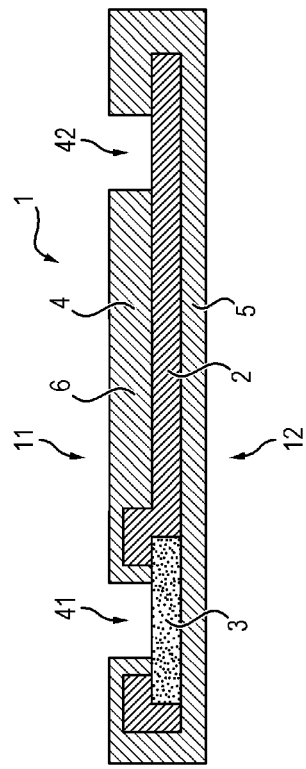
FIG. 2 represents a simplified sectional view of an implant according to a first embodiment of the invention.
Figure 4:
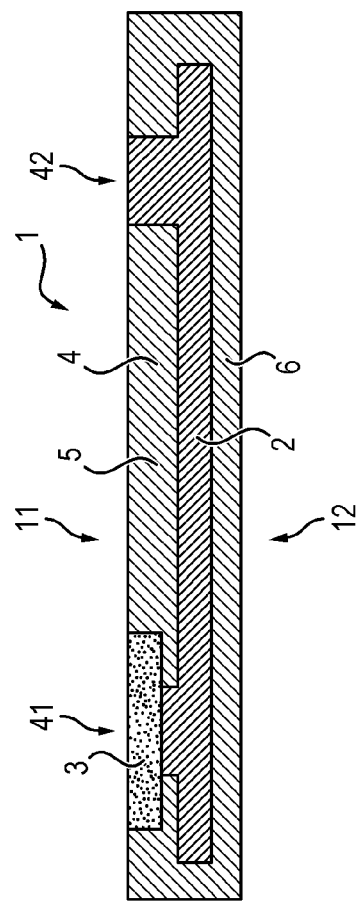
FIG. 4 represents a simplified sectional view of an implant according to a second embodiment of the invention.

As shown in FIG. 2, which represents a flexible soft implant 1 according to a first embodiment, and in FIG. 4, which represents the flexible soft implant 1 in a second embodiment, said flexible soft implant 1 comprises:
- an electrically conductive layer 2, which can be made of metal or electrically conductive doped diamond;
- one or more electrodes 3, made of electrically conductive doped diamond, for example doped with boron or phosphorus, each in contact with the electrically conductive layer 2, said electrically conductive layer 2 thus presenting an electrical track per electrode 3 of the implant;
- a protective coating 4 of electrically insulating diamond, typically intrinsic (i.e. undoped) diamond, which encapsulates/surrounds the electrically conductive layer 2 and the electrode(s) 3 except at the areas 41 and 42 of each electrode.

The protective coating 4 includes a first opening 41 at each electrode 3 to allow each electrode 3 to be coupled with the desired nerve structure. The protective coating 4 also includes a second opening 42 at the electrically conductive layer 2 to form an electrical contact area for an electrode, thereby allowing the flexible soft implant 1 to be connected to an electronic component to control the electrical coupling between the electrode 3 and the nerve structure.

The flexible soft implant 1 comprises a front side 11 on which the first opening 41 and the second opening 42 are located, and a back side 12 which is opposite said front side 11.

The fact that the protective coating 4 is made of electrically non-conductive diamond and the electrode 3 is made of electrically conductive doped diamond ensures long-term protection of the electrically conductive layer 2, which is completely encapsulated by diamond (except at the second opening 42 which is not in contact with biological tissue), the diamond being perfectly impermeable because the density of the diamond prevents the particles from diffusing through it. In addition, diamond offers the advantage of being biocompatible, and can therefore be implanted in the human body.

In addition, the impermeability of the flexible soft implant 1 is ensured by the fact that the contacts between the electrode 3 and the protective coating 4 are areas of epitaxial regrowth of the electrode 3 on the protective coating 4, and of the protective coating 4 on the electrode 3. Such regrowth ensures that there is no discontinuity between the electrode 3 and the protective coating 4, thus guaranteeing the impermeability of the implant 1.

In addition, as shown in FIG. 14, the implant 1 is highly flexible, allowing said implant 1 to follow the different asperities of the surface on which said implant is positioned. Such flexibility with an implant comprising a protective diamond coating 4 is surprising because diamond is a rigid material. The flexibility of the implant is due in particular to its very low thickness.

For simplification purposes, the implant 1 is described with one electrode 3, but the implant 1 preferably comprises a plurality of electrodes 3 in contact with the electrically conductive layer 2, said electrically conductive layer 2 forming an electrical track for each electrode 3 of the implant.

As shown in FIG. 2, the flexible soft implant 1 according to the first embodiment comprises a first electrically insulating diamond layer 5 which is in contact with the diamond electrode 3 and the electrically conductive layer 2, the first layer 5 forming a first part of the protective coating 4. The implant 1 also comprises a second electrically insulating diamond layer 6 which is in contact with the diamond electrode 3 and the electrically conductive layer 2, the second layer 6 forming a second part of the protective coating 4. The first layer 5 and the second layer 6 are also in contact wherever the electrodes 3 and the electrically conductive layer 2 are not present. The terms first layer 5 and second layer 6 refer here to the order in which the layers 5 and 6 are manufactured.

The second layer 6 is located on the front side 11 of the implant 1 and thus comprises the first opening 41 and the second opening 42, the first layer 5 being located on the back side 12 of said implant 1.

The electrically conductive layer 2 is encapsulated (bounded or located enclosed, enveloped, surrounded or coated) by the electrode 3, by the first layer 5 and by the second layer 6, at the electrode 3, and by the first layer 5 and the second layer 6 over its entire remaining surface (length, width and thickness) except for the area defining the electrical contact because of the second opening 42. In addition, at the electrode 3, the electrically conductive layer 2 is encapsulated by the electrode 3 and the second layer 6.

The electrode 3 is made by regrowth from the first layer 5, and the second layer 6 is made by regrowth from the electrode 3, thus ensuring the impermeability of the flexible soft implant 1.

The electrode 3 is encapsulated (or bounded or located enclosed, enveloped, surrounded or coated) by the first layer 5, by the second layer 6, and by the electrically conductive layer 2, except for a central measuring part corresponding to the first opening 41.

As shown in FIGS. 3a and 3b, the flexible soft implant 1 may comprise a layer of polymer, preferably biocompatible polymer, which is located on the back side 12 and/or on the front side 11 of the flexible soft implant 1.

This polymer layer makes the flexible soft implant 1 easier to handle, especially by the doctor when the implant 1 is implanted, as the flexibility and thinness of the implant 1 may make it difficult to handle.

The polymer can be biodegradable in order to be removed after implantation of flexible soft implant 1 in the patient's body, the polymer being useful only when implanting the flexible soft implant 1.

In the variant shown in FIG. 3a, the implant 1 comprises a first outer polymer layer 71 which is located on the back side 12 of said implant 1.

In the variant shown in FIG. 3b, in addition to having the first outer polymer layer 71 on its back side 12, the implant 1 has a second outer polymer layer 72 on its front side 11. The second outer polymer layer 72 has openings opposite the first opening 41 and the second opening 42 to maintain access to the electrode 3 and to the electrical contact area. Thus, in this variant the implant is completely encapsulated by polymer, except for the measuring part of the electrode 3 and the electrical contact area.

The polymer layer(s) deposited on the implant 1 should preferably be between 2 and 10 µm thick, in order to facilitate the handling of the implant 1 while keeping the implant 1 with satisfactory flexibility.

As shown in FIG. 4, the implant 1 according to the second embodiment also comprises a first electrically insulating diamond layer 5 which is in contact with the electrode 3 and the electrically conductive layer 2, the first layer 5 forming a first part of the protective coating 4. The implant 1 also comprises a second electrically insulating diamond layer 6 which is in contact with the electrode 3 and the electrically conductive layer 2, the second layer 6 forming a second part of the protective coating 4. The first layer 5 and the second layer 6 are also in contact with each other wherever the electrodes 3 and the electrically conductive layer 2 are not present. Again, the terms first layer 5 and second layer 6 refer here to the order in which the layers 5 and 6 are manufactured.

The first layer 5 is located on the front side 11 of the implant 1 and thus includes the first opening 41 and the second opening 42, while the second layer 6 is located on the back side 12.

In this embodiment, the electrically conductive layer 2 is encapsulated by the electrode 3 and by the first and second diamond layers 5 and 6 at the electrode 3 and over its entire remaining surface (length, width and thickness) by the first and second diamond layers 5 and 6, except for the area defining the electrical contact. In addition, at the electrode 3, the electrically conductive layer 2 is encapsulated by the electrode 3 and the first and second diamond layers 5 and 6, the first layer 5 being produced by regrowth from the electrode 3.

According to the second embodiment, electrode 3 has its coupling side, the side intended to face the nerve structure, which is flush with the first layer 5 over its entire surface.

Figure 5:
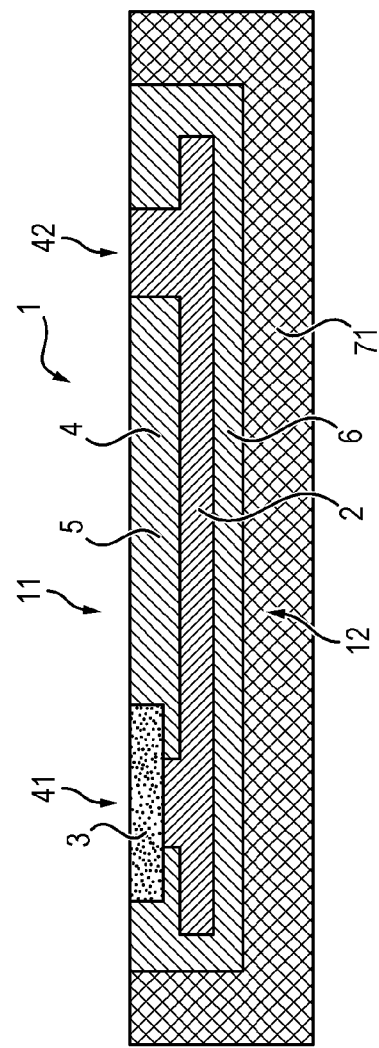
FIG. 5 shows an implant according to the second embodiment comprising a polymer layer on its back side.

As shown in FIG. 5, the implant 1 according to the second embodiment may also include a layer of polymer, preferably biocompatible polymer, which is located on the back side 12 of the flexible soft implant 1.

Again, the polymer can be biodegradable so that it can be removed after the implant 1 is implanted in the patient's body, the polymer being useful only when the implant 1 is implanted.

In the variant shown in FIG. 5, which is a variant similar to that shown in FIG. 3a, the implant 1 comprises the first outer polymer layer 71 which is located on the back side 12 of said implant 1.

The polymer layer(s) deposited on the implant 1 should preferably be between 2 and 10 µm thick, in order to facilitate the handling of the implant 1 while keeping the implant 1 with satisfactory flexibility.

For both embodiments, the electrode 3, the first layer 5 and the second layer 6 are each less than 500 nm and maximum 1 μm thick, thus allowing the implant 1 to be highly flexible, despite the fact that the electrode 3, the first layer 5 and the second layer 6 are made of diamond.

In addition, for both embodiments, the electrically conductive layer 2 is less than 3 μm thick, to ensure the flexibility of the implant.

Moreover, for both embodiments, the electrode 3 is preferably nanostructured in order to increase the signal-to-noise ratio. The side of the electrode 3 intended to face the nerve structure is not smooth, but has a nanometric relief, so as to increase the surface area of this side of the electrode 3 facing the nerve structure.

The nanostructuring of the electrode 3, or in other words, giving a nano-sized relief to one side of the electrode 3, can be done as follows:
- a material forming a nanostructured 3D pattern is deposited on one side of the electrode 3;
- an electrically conductive doped diamond layer is deposited over the material forming the 3D pattern, so that the electrode 3 is re-formed with a side that follows the 3D pattern of the material, and is thus nanostructured. Doped diamond can for example be deposited by chemical vapor deposition (CVD), in which case the material comprising the 3D pattern must be able to withstand the high temperature required for the growth of a diamond layer by CVD.

According to a first possible example for producing the electrode 3 with a nanostructured side, after growing doped diamond to form the electrode 3, a polymer foam, such as polypyrrole, is deposited on the side of the electrode 3 intended to form the coupling side with the nerve structure. Then a layer of doped diamond is formed on the polymer foam, this layer of doped diamond is nanostructured because it conforms to the very uneven relief of the polymer foam and forms a three-dimensional (3D) pattern.

According to another possible example for producing the electrode 3 with a nanostructured side, after growing doped diamond to form the electrode 3, carbon nanotubes are deposited on the side of the electrode 3 intended to form the coupling side with the nerve structure. Next, a doped diamond layer is formed on the carbon nanotubes, this doped diamond layer is nanostructured because it conforms to the very uneven relief of nanometric dimension created by the carbon nanotubes and forms a three-dimensional (3D) pattern.

The electrode 3 can of course be nanostructured by depositing other conductive materials that also have high porosity and good resistance to the growth conditions of synthetic diamond.

Figure 6:
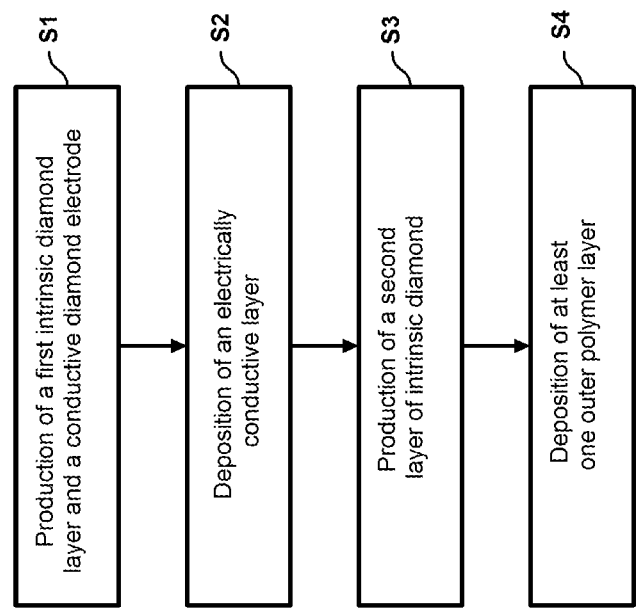
FIG. 6 shows a schematic representation of the steps of a process for manufacturing the implant.

The flexible soft implant 1 according to any one of the previously presented embodiments can be obtained by the manufacturing process shown in FIG. 6, which comprises the following steps:
- S1: producing a first electrically insulating diamond layer 5 and at least one electrically conductive doped diamond electrode 3 by epitaxial growth, the electrode 3 and the first layer 5 being deposited one on top of the other by epitaxial regrowth at the end of this step S1;
- S2: depositing an electrically conductive layer 2 abutting at least part of the electrode 3 and at least part of the first layer 5, thus defining a conductive track for the electrode 3;
- S3: producing a second electrically insulating diamond layer 6 supported on at least part of the electrically conductive layer 2, and at least on part of the remaining part of the first layer 5, by epitaxial growth.

The steps of the process are carried out so that:
- an electrically insulating diamond/electrically conductive doped diamond seal is produced at the electrode by epitaxial regrowth,
- the electrically conductive layer 2 is encapsulated by the electrically conductive doped diamond electrode 3, by the first electrically insulating diamond layer 5 and by the second electrically insulating diamond layer 6, at the electrode 3 and over its entire remaining surface (length, width and thickness), except for an area defining an electrical contact (this area corresponding to the second opening 42).

The process may also include a step S4 of depositing at least one outer polymer layer, for example on the back side 12 of the implant 1 or the front side 11 of the implant 1.

In a possible variant of step S4 shown in FIG. 7, in which two polymer layers are deposited on the front side 11 of the implant 1 as well as on the back side 12 of the flexible soft implant 1, step S4 comprises the following steps:
- S41: depositing a polymer layer on the front side 11 of the flexible soft implant 1, where the electrode 3 and the associated electrical contact formed by the electrically conductive layer 2 are located, as well as on the substrate on which the implant is manufactured. The polymer layer deposited in this step is the second outer polymer layer 72.
- S42: opening the polymer layer at the electrical contact and the electrode 3, thus opening the polymer layer at the first opening 41 and the second opening 42, and depositing a protective resin.
- S43: etching the substrate until the back side 12 of the flexible soft implant 1 is uncovered.
- S44: depositing another polymer layer on the back side 12 of the flexible soft implant 1. The polymer layer deposited in this step corresponds to the first outer polymer layer 71; removal of the protective resin and cutting of the implant to give it its final shape.

A possible first implementation of the manufacturing process for producing an implant 1 according to the first embodiment is illustrated in FIGS. 8a-8h.

As shown in FIG. 8a, a substrate S is provided at the beginning of the manufacturing process in order to carry out the succession of deposition steps of the different layers forming the flexible soft implant 1.

In the first implementation of the process, as shown in FIG. 8b, the formation of the first electrically insulating diamond layer 5 is carried out first. The first electrically insulating diamond layer 5 is produced by depositing a layer of diamond nanoparticles on the substrate which serve as nucleation sites for the epitaxial growth of diamond. The growth of the first layer 5 is then carried out by chemical vapor deposition (CVD). Since growth for diamond is done at high temperatures, it is preferable that the substrate S is made of silicon, or quartz, rather than polymer.

In order to determine the area on which the first layer 5 is formed, several solutions are possible. For example, it is possible to deposit the diamond nanoparticles on the entire substrate S and then to remove the diamond nanoparticles by etching in the areas on which it is not desired that the first layer 5 is formed, while the area of interest is protected from etching by a mask which protects the diamond nanoparticles on this area of interest. It is also possible to deposit the diamond nanoparticles only on the area of interest by covering the areas on which it is not desired for the first layer 5 to be formed by a mask when depositing the diamond nanoparticles.

Then, as shown in FIG. 8c, the electrode 3 is formed by creating an electrically conductive doped diamond layer on top of the first electrically insulating diamond layer 5. The electrode 3 is formed by epitaxial regrowth from the first layer 5, thus achieving material continuity between the two diamond layers.

In order to determine the area on which electrode 3 is formed, several solutions are possible. For example, it is possible to deposit the diamond nanoparticles on the entire layer 5 and the substrate S, and then to remove the diamond nanoparticles by etching in the areas on which it is not desired that the electrode 3 is formed, while the area of interest is protected from etching by a mask which protects the diamond nanoparticles on this area of interest. It is also possible to deposit the diamond nanoparticles only on the area of interest by covering the areas on which it is not desired for the electrode 3 to be formed by a mask when depositing the diamond nanoparticles.

The electrode 3 can be nanostructured in this step, for example by one of the methods described above.

As shown in FIG. 8d, the electrically conductive layer 2 is then formed on the first layer 5 as well as on the outer contour of the electrode 3. The electrically conductive layer 2 is formed by depositing a metal layer, for example by chemical vapor deposition. The electrically conductive layer 2 can also be formed by depositing an electrically conductive doped diamond layer. The electrically conductive layer 2 is formed so as to form an electrical track for the electrode 3, thereby connecting said electrode 3 to an electrical component. Again, control of the shape of the electrically conductive layer 2 is carried out by using a mask.

Figure 8E:
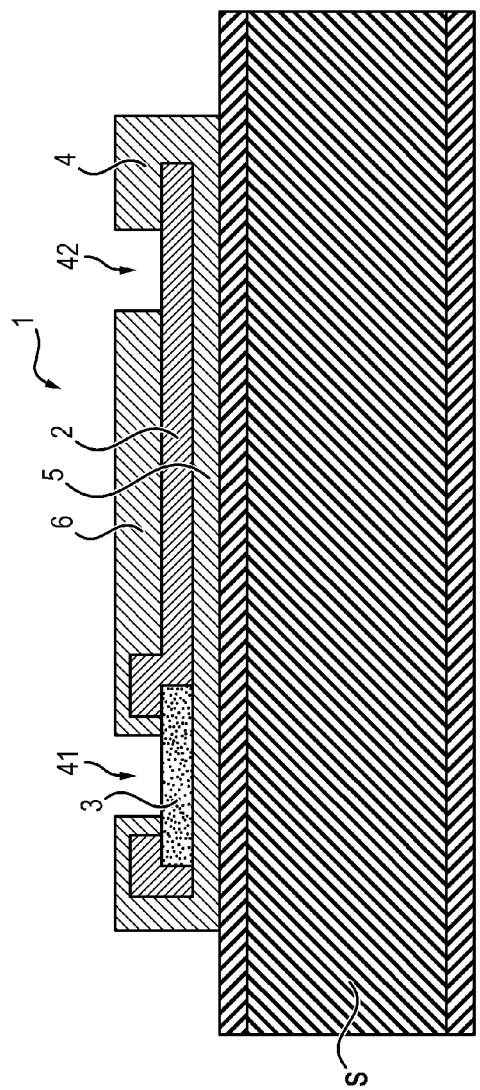

As shown in FIG. 8e, the second electrically insulating diamond layer 6 is then formed over the assembly made in the previous steps, thus completing the formation of the protective coating 4 around the electrically conductive layer 2. However, the second layer 6 is not deposited on the central area of the electrode 3, thus forming the first opening 41, nor on an area of the electrically conductive layer intended to form an electrical contact area, thus forming the second opening 42. The second layer 6 is produced by epitaxial growth from the electrode 3 and the first layer 5 as well as by epitaxial growth from diamond nanoparticles deposited on the electrically conductive layer 2. It should be noted that the diamond nanoparticles for the formation of the second layer 6 can also be deposited on the first layer 5 and the electrode 3, said diamond nanoparticles not influencing epitaxial regrowth from the first layer and the electrode 3. After this step, the implant 1 is formed on the substrate S.

Figure 8F:
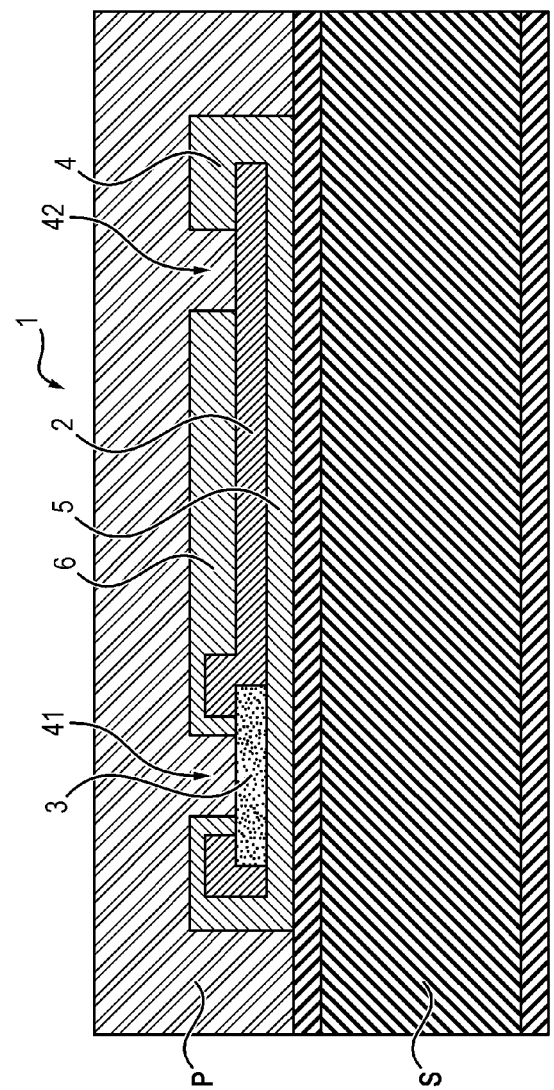

As shown in FIG. 8f, a protective layer P is deposited on the implant 1 to protect the implant 1 during the removal of the substrate S. The protective layer P can be, for example, a film with an adhesive or resin.

As shown in FIG. 8g, the substrate S is removed, for example by etching, thus freeing the back side 12 of the implant 1.

As shown in FIG. 8h, the protective layer P is then removed, freeing the front side 11 of the implant 1.

When the protective layer P is a film with an adhesive, the protective layer P can be removed by exposing it to UV radiation which removes its adhesion to the adhesive, and then placing the implant 1 in an ethanol solution to remove the film.

When the protective layer P is a resin, said protective layer P can be removed with a solvent.

In addition, as mentioned above, the implant 1 may include a polymer layer to facilitate the handling of said implant 1.

As shown in FIG. 9a, the first outer polymer layer 71 can be deposited on the back side 12 of the implant after removal of the substrate S (for example after the step shown in FIG. 8g).

As shown in FIG. 9b, the protective layer P is then removed from the front side 11 of the implant 1.

As shown in FIG. 10a, in the variant in which the implant 1 comprises the first outer polymer layer 71 and the second outer polymer layer 72, the second outer polymer layer 72 is deposited on the first front side 11 of the implant after the deposition of the second electrically insulating diamond layer 6 (for example after the step shown in FIG. 8e). The second outer polymer layer 72 is etched at the first opening 41 and the second opening 42 to leave said openings in communication with the outside.

The protective layer P is then deposited on the second outer polymer layer 72, as shown in FIG. 10b.

Figure 10C:
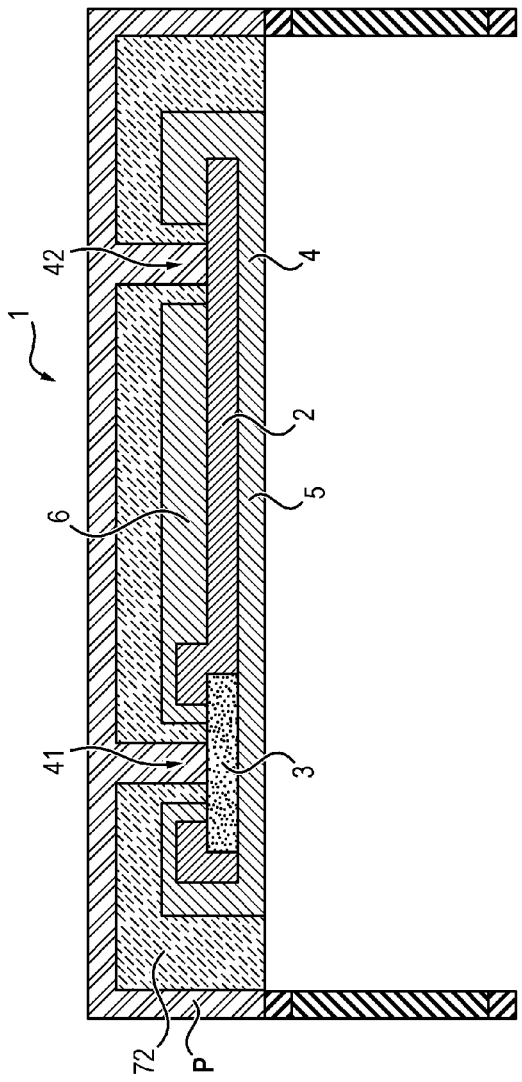
Figure 10D:
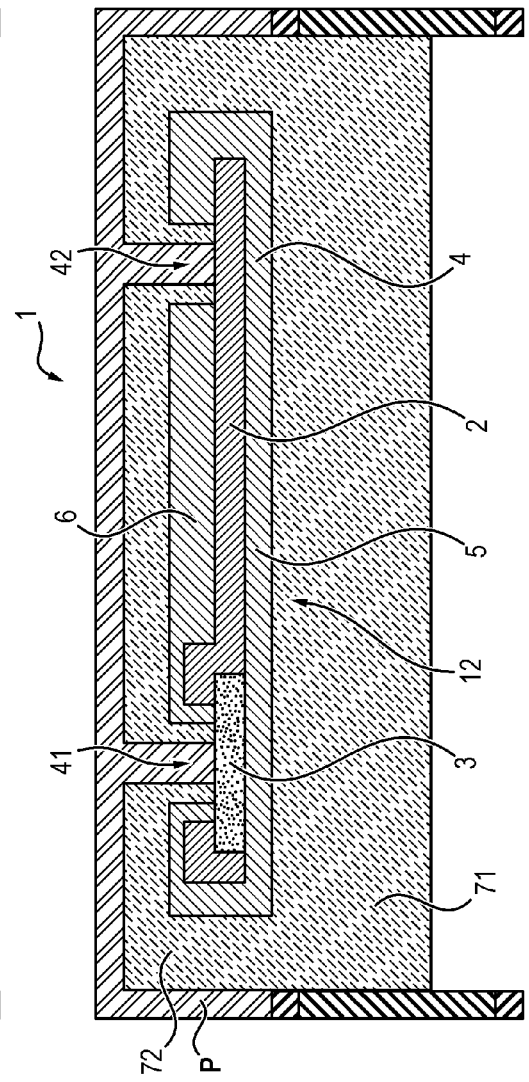
Figure 10E:
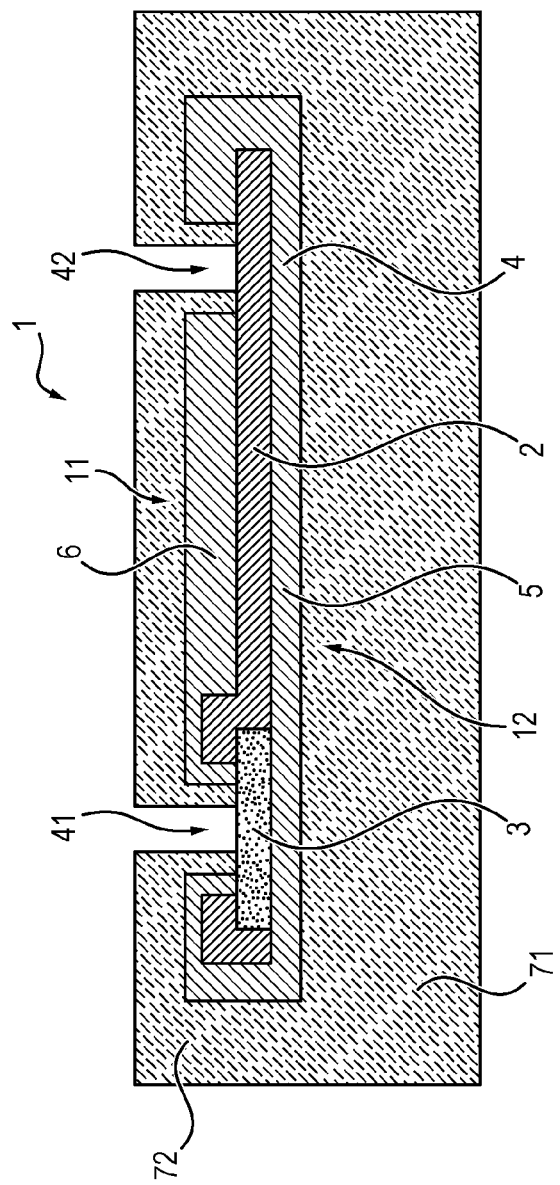

Then, in a manner similar to the variant in FIGS. 9a and 9b, and as shown in FIGS. 10c, 10d and 10e, the substrate S is removed, the first outer polymer layer 71 is deposited on the back side 12 of the flexible soft implant 1, and the protective layer P is removed from the front side 11 of the flexible soft implant 1.

A possible second implementation of the manufacturing process for producing an implant 1 according to the second embodiment is shown in FIGS. 11a-11h.

Figure 11A:
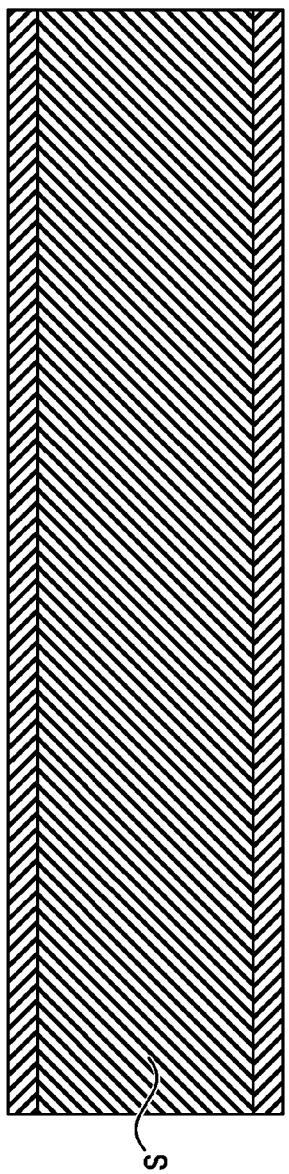

As shown in FIG. 11a, a substrate S is provided at the beginning of the manufacturing process in order to carry out the succession of deposition steps of the different layers forming the flexible soft implant 1.

Figure 11B:
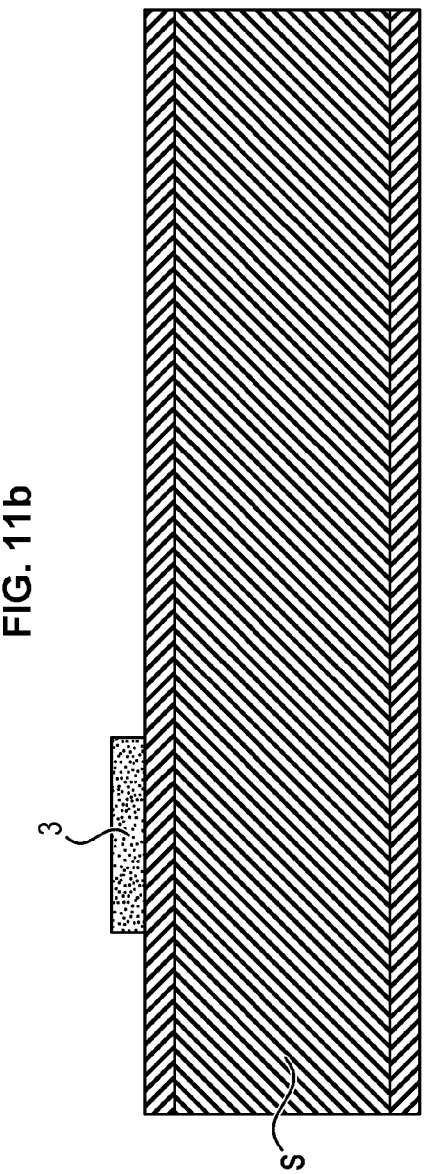

In the second implementation of the process, as shown in FIG. 11b, the formation of the electrically conductive doped diamond electrode 3 is carried out first. The electrode 3 is formed directly on the substrate S. The electrically conductive doped diamond electrode 3 is formed by depositing a layer of nanoparticles of diamond which serve as a starting point for the epitaxial growth of diamond. The growth of the doped diamond electrode 3 is then carried out by chemical vapor deposition (CVD). Since growth for diamond is done at high temperatures, it is preferable that the substrate S be made of silicon, or quartz, rather than polymer. The diamond for the electrode 3 can be boron or phosphorus.

In order to determine the area on which the electrode 3 is formed, several solutions are possible. For example, it is possible to deposit the diamond nanoparticles on the entire substrate S and then remove the diamond nanoparticles by etching in the areas on which it is not desired for the electrode 3 to be formed, while the area of interest is protected from etching by a mask which protects the diamond nanoparticles on this area of interest. It is also possible to deposit the diamond nanoparticles only on the area of interest by covering the areas on which it is not desired for the electrode 3 to be formed by a mask when depositing the diamond nanoparticles.

Figure 11E:
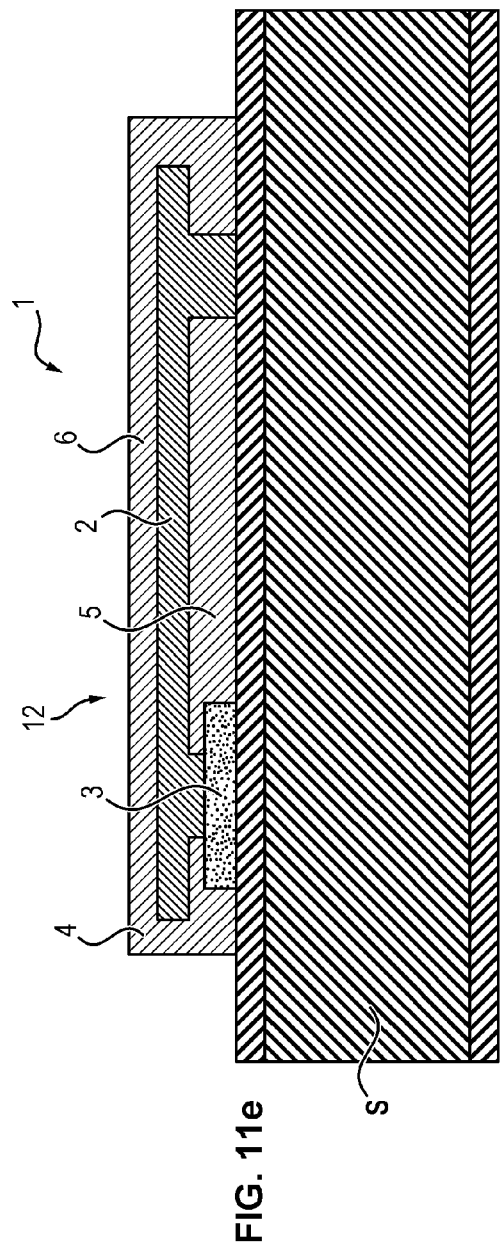

Then, as shown in FIG. 11e, the first layer 5 is formed by creating an electrically insulating diamond layer on one part of the substrate and on the outer contour of the electrode 3. The first layer 5 is formed by epitaxial regrowth from the electrode 3, thus achieving material continuity between the two diamond layers. The deposition of the electrically insulating diamond layer to form the first layer 5 is carried out with a mask so that, on the one hand, the first layer 5 does not cover electrode 3 on a central part of the electrode 3, in order to allow contact between the electrode and the electrically conductive layer 2, and, on the other hand, in order to form the second opening 42 for the creation of the area defining an electrical contact.

As shown in FIG. 11*d*, the electrically conductive layer 2 is then formed on top of the first layer 5. The electrically conductive layer 2 is in contact with the central part of the electrode 3 not covered by the first layer 5. The electrically conductive layer 2 is also in contact with the substrate S at the second opening 42 formed in the first layer 5, thereby defining an electrical contact. The electrically conductive layer 2 is formed by depositing a metal layer, for example by chemical vapor deposition. The electrically conductive layer 2 can also be formed by depositing an electrically conductive doped diamond layer. The electrically conductive layer 2 is formed so as to form an electrical track for the electrode 3, thereby connecting said electrode 3 to an electrical component. Again, control of the shape of the electrically conductive layer 2 is carried out by using a mask.

As shown in FIG. 11*e*, the second electrically insulating diamond layer 6 is then formed over the assembly made in the previous steps, thus completing the formation of the protective coating 4 around the electrically conductive layer 2. The second layer 6 completely covers the electrically conductive layer 2. The second layer 6 is produced by epitaxial growth from the first layer 5 as well as by epitaxial growth from diamond nanoparticles deposited on the electrically conductive layer 2. At the end of this step, the implant 1 is formed on the substrate S, the front side 11 of the implant 1 being against the substrate S, and the back side 12 of the implant 1 being directed outwards.

Figure 11F:
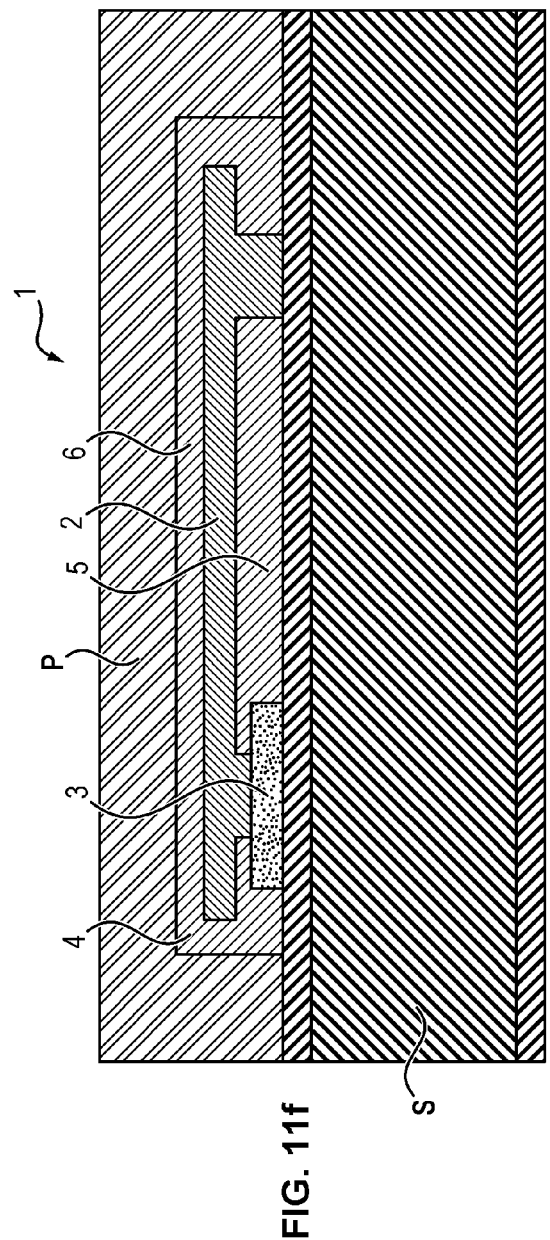

As shown in FIG. 11*f*, a protective layer P is deposited on the back side 12 of the implant 1 to protect the implant 1 during the removal of the substrate S. The protective layer P can be, for example, a film comprising an adhesive or resin.

As shown in FIG. 11*g*, the substrate S is removed, for example by etching, freeing the front side 11 of the implant 1.

As shown in FIG. 11*h*, the protective layer P is then removed, freeing the back side 12 of the implant 1.

When the protective layer P is a film with an adhesive, the protective layer P can be removed by exposing it to UV radiation which removes its adhesion to the adhesive, and then placing the implant 1 in an ethanol solution to remove the film.

When the protective layer P is a resin, said protective layer P can be removed with a solvent.

In addition, as mentioned above, the implant 1 may include a polymer layer to facilitate the handling of said implant 1.

As shown in FIG. 12, the first outer polymer layer 71 can be deposited on the back side 12 of the implant before the deposition of the protective layer P (for example after the step shown in FIG. 11*e*).

The substrate S and the protective layer P are then removed, as shown in FIG. 11*g* and FIG. 11*h*.

FIGS. 13*a*-13*g* represent the top views of the different steps of the first implementation of the manufacturing process shown in FIGS. 8*a*-8*e* and 10*a*-10*d*. The shape of the implant 1 shown in these figures is only one possible example of the shape that can be given to the implant 1.

Figure 13A:
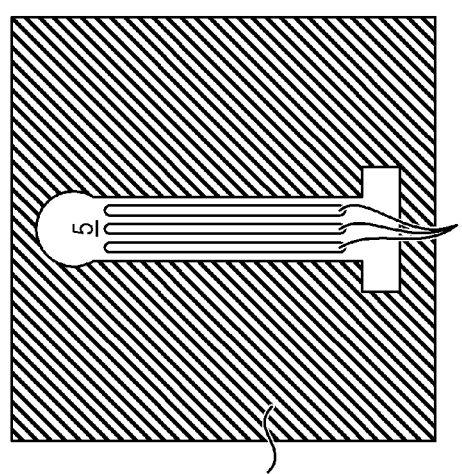

FIG. 13*a* corresponds to the first electrically insulating diamond layer 5 deposited on the substrate, and is therefore a top view of FIG. 8*a*.

Here this first layer 5 of insulating diamond has a desired thickness and surface shape perpendicular to the thickness.

Figure 13B:
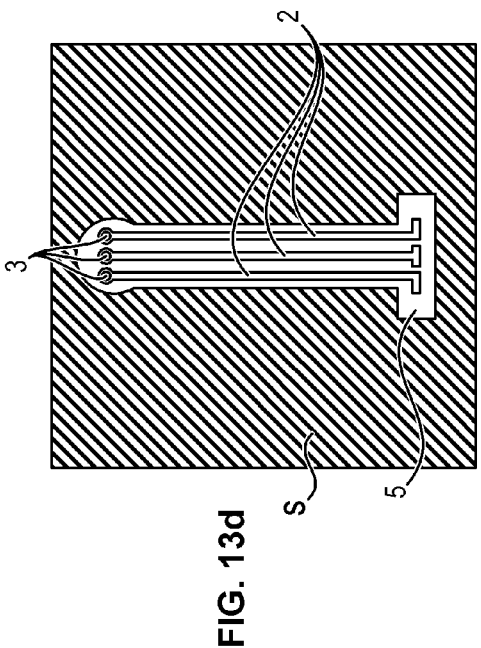

FIG. 13*b* corresponds to a variant of FIG. 13*a*, in which the first layer 5 has grooves 51 to increase the flexibility of the implant 1.

Figure 13C:
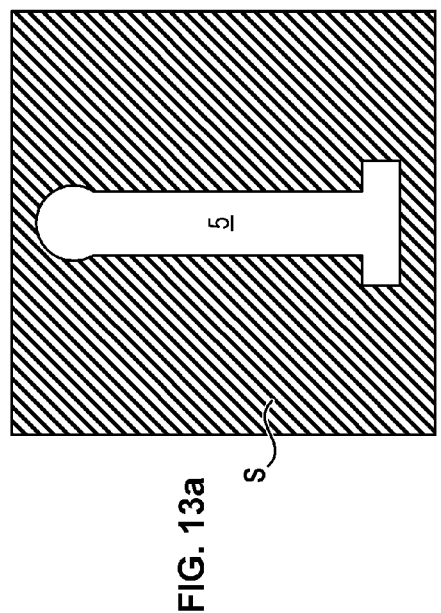

FIG. 13*c* corresponds to the step in which the electrode 3 is formed on the first layer 5 by epitaxial regrowth. In the variant shown in FIG. 13*c*, three electrodes 3 are formed.

Figure 13D:
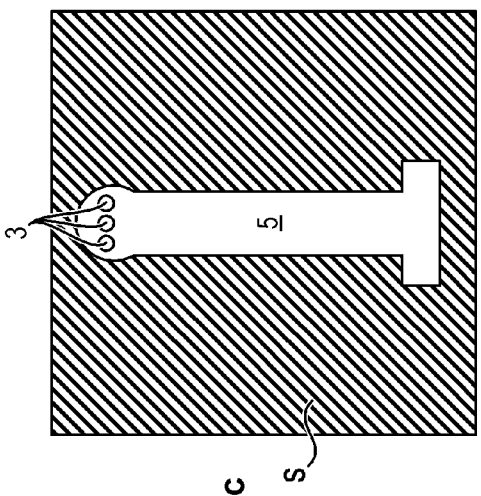

FIG. 13*d* corresponds to the step in which the electrically conductive layer 2 is formed on the first layer 5 and on the electrode 3. Since the implant 1 comprises three electrodes 3, the electrically conductive layer 2 forms three electrical tracks, one track for each electrode 3.

Figure 13F:
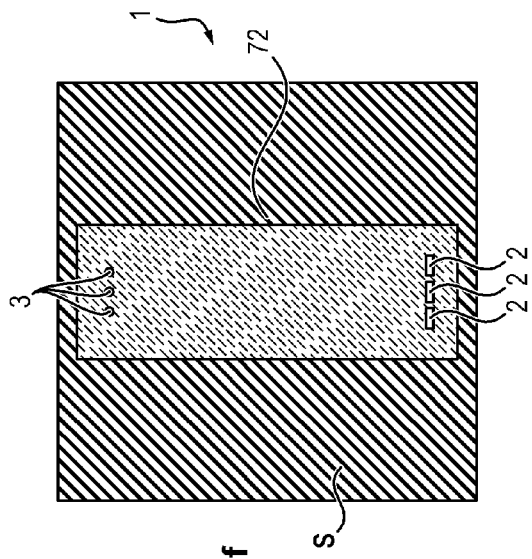
Figure 13G:
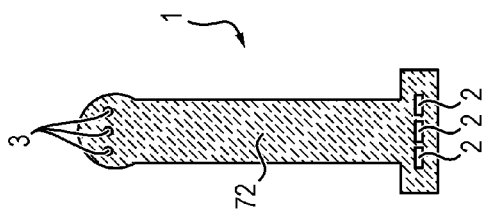
Figure 13E:
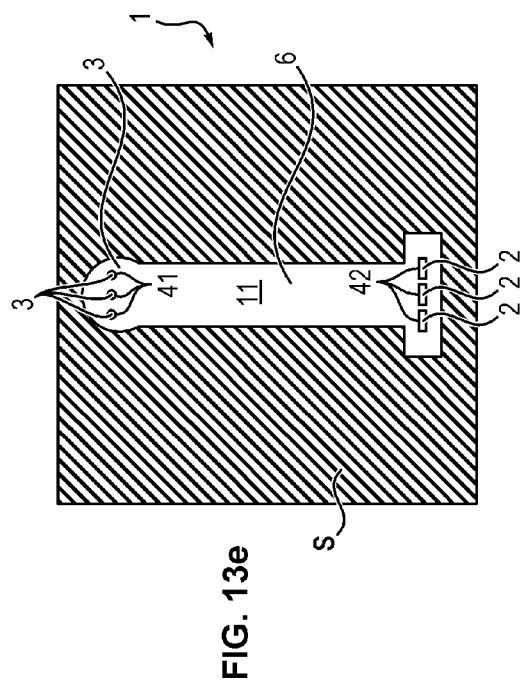

FIG. 13*e* corresponds to the step in which the second electrically insulating diamond layer 6 is formed by epitaxial regrowth from the electrode 3 and the first layer 5 so as to seal the electrically conductive layer 2. The electrodes 3 are visible through the first openings 41, a first opening 41 for each electrode 3, and each track formed by the electrically conductive layer 2 is visible through the second openings 42, a second opening 42 for each track.

Similarly, the second layer 6 of insulating diamond has a desired thickness and surface shape perpendicular to the thickness.

FIG. 13*f* shows the step in which the front side 11 of the implant 1 is covered by the second outer polymer layer 72. The electrodes 3 and the electrically conductive layer 2 are accessible through the openings formed in the second outer polymer layer 72.

FIG. 13*g* shows the step in which the substrate S and the protective layer P were removed, thus separating the implant 1 from the wafer. Like the first and second diamond layers 5 and 6, the second outer polymer layer 72 is cut to give the final shape to the implant.

As can be seen in FIGS. 14, the flexible soft implant 1 according to the invention has a flexibility that allows it to adapt to the shape of the surface on which it is deposited, even if the surface is very uneven. FIGS. 14 show the flexible soft implant 1 located on one hand in a latex glove G simulating the surface of a nerve structure. The surface of the glove has bulges/folds B, and the shape of the implant 1 follows the shape of the bulges/folds B of the fingers and the back of the hand. The flexible soft implant 1, which is then placed back on a table, can return to its flat shape on the flat surface of the table.

The flexibility of the implant according to the invention is comparable to that of implants of the prior art which do not include intrinsic diamond layers of encapsulation of the conductive track.

Thus, the total thickness and geometry of the implant 1 are adapted so that the flexible soft implant 1 hugs the surface of the organ of interest, such as the cortical cortex, the heart, or a muscle, the total thickness of the implant being less than 20 µm.

The total thickness is equal to=thickness of the electrical layer 2+thickness of the electrically insulating diamond layers 5 and 6+thickness of the outer polymer layer 72+thickness of the outer polymer layer 71.

The total thickness is so small that the implant, although it contains diamond (to ensure a high seal and therefore a high robustness of the implant over time), is extremely flexible and can be deformed as desired to take the shape of the element on which it is placed.

The invention claimed is:
1. A flexible soft implant for focal stimulation or electrical recording of a nerve structure of an organ of interest, comprising:
   an outer layer of biocompatible polymer, a first layer of electrically insulating diamond connected to the outer layer a second layer of electrically insulating diamond in contact with the first layer, the second layer comprising a first opening and a second opening, an electrically conductive doped diamond electrode covered by the first layer and the second layer, the electrode being uncovered by the second layer at the first opening so as to allow the electrode to be coupled with the nerve structure, an electrically conductive layer comprising one of a metal or an electrically conductive doped diamond, the conductive layer being in contact with the electrode and the first layer, the conductive layer defining a conductive track, a protective coating comprising the first layer and the second layer, contacts between the electrode and the protective coating being areas of epitaxial regrowth of the electrode on the protective coating, the flexible soft implant being arranged so that the conductive layer is encapsulated by the electrode, the first layer, and the second layer, the conductive layer being uncovered by the second layer at the second opening so as to define an electrical connection for connecting the flexible soft implant via the conductive layer to an electronic component, the flexible soft implant comprising a front side, the front side comprising the second layer;

the flexible soft implant comprising a back side, the back side comprising the first layer;

the first layer, the electrode, and the second layer each having thicknesses of less than 500 nm, the conductive layer having a thickness of less than 3 μm, a total thickness and &geometry of the flexible soft implant being configured so that the flexible soft implant conforms to a surface of the organ of interest, the total thickness of the flexible soft implant being less than 20 μm.

2. The flexible soft implant of claim 1, wherein at the electrode, the conductive layer is encapsulated by the electrode, the second layer being obtained by epitaxial regrowth from the electrode, the electrode being encapsulated, except on the first opening, by the first layer, by the second layer and by the conductive layer.

3. The flexible soft implant of claim 1, wherein the conductive layer is encapsulated by the electrode and the first layer and the second layer, the first layer being obtained by epitaxial regrowth from the electrode.

4. The flexible soft implant of claim 3, wherein the first outer layer and the second outer layer have a thickness of between 2 μm and 10 μm.

5. The flexible soft implant of claim 3, wherein the first outer layer and the second outer layer are made of a biodegradable polymer.

6. The flexible soft implant of claim 1, wherein the outer layer is located on the back side of the implant.

7. The flexible soft implant of claim 6, wherein the outer layer is a first outer layer, the implant comprising a second outer layer of polymer located on the front side so that the first outer layer and the second outer layer completely surround the implant except at the first opening and at the second opening.

8. The flexible soft implant of claim 1, wherein the electrode is nanostructured.

9. The flexible soft implant of claim 1, wherein the total thickness of the flexible soft implant being less than 10 μm.

10. The flexible soft implant of claim 1, wherein the diamond of the following elements: electrode, first layer, second layer, and conductive layer when made of diamond, is not ultrananocrystalline (UNCD).

11. The flexible soft implant of claim 1, wherein the diamond for the electrode is doped with boron or phosphorus.

12. The flexible soft implant of claim 1, wherein a ratio of a length between the first opening and the second opening to the thickness of the implant is greater than 100.

13. A process for manufacturing the flexible soft implant of claim 1 from a substrate, comprising:
    producing the electrode and one of the first layer and the second layer by epitaxial growth, the electrode and the one of the first layer and the second layer being deposited one on top of the other by epitaxial regrowth;
    depositing the conductive layer on the electrode and on the one of the first layer and the second layer;
    producing the other of the first layer and the second layer on the conductive layer and the one of the first layer and the second layer by epitaxial growth;
    wherein the process is carried out so that
    contacts between the electrode and the protective coating are areas of epitaxial regrowth of the electrode on the protective coating, and
    the conductive layer is encapsulated by the electrode, the first layer, and the second layer, the conductive layer being uncovered by the second layer at the second opening so as to define an electrical connection for connecting the flexible soft implant via the conductive layer to an electronic component.

14. The process of claim 13, wherein:
    the one of the first layer and the second layer is the first layer,
    in the step of producing the first layer, producing the first layer on the substrate by epitaxial growth, then producing the electrode,
    in the step of depositing the conductive layer, depositing the conductive layer on an outer contour of the electrode and on the first layer, and
    in the step of producing the second layer, epitaxial growth of the second layer is performed by epitaxial regrowth on
    the conductive layer except on the second opening and on the electrode except on the first opening.

15. The process of claim 13, wherein:
    the one of the first layer and the second layer is the second layer,
    in the step of producing the second layer, producing the electrode on the substrate by epitaxial growth,
    then producing the second layer on the outer contour of the electrode by epitaxial regrowth and on the substrate by epitaxial growth except in a area which defines the first opening,
    in the step of depositing the conductive layer, depositing the conductive layer on the electrode and on the second layer.

16. The process of claim 13, further comprising the step of depositing the outer layer on the back side of the implant.

17. The process of claim 16, further comprising the steps:
    depositing a second outer layer of polymer on the front side of the implant and on the substrate;
    opening the second outer layer at the first opening and at the second opening and depositing a protective resin;
    etching the substrate until the back side of the implant is exposed;

depositing a third outer layer of polymer on the back side of the implant, removing the protective resin and cutting the implant to obtain a final shape.

18. The process of claim 13, wherein the electrode is nanostructured as follows:
 a material forming a nanostructured 3D pattern is deposited on the electrode;
 an electrically conductive doped diamond layer is deposited over the material forming the nanostructured pattern.

* * * * *